US010258398B2

(12) United States Patent
Arthur et al.

(10) Patent No.: US 10,258,398 B2
(45) Date of Patent: Apr. 16, 2019

(54) DEVICE FOR PERFORMING A SURGICAL PROCEDURE AND METHOD (71) Applicant: Medtronic Holding Company Sàrl, Tolochenaz (CH)

(72) Inventors: Amy L. Arthur, Mountain View, CA (US); Mojan Goshayeshgar, Atherton, CA (US)

(73) Assignee: Medtronic Holding Company Sàrl, Tolochenaz (CH)

( * ) Notice: Subject to any disclaimer, the term of this patent is extended or adjusted under 35 U.S.C. 154(b) by 654 days.

(21) Appl. No.: 15/046,654

(22) Filed: Feb. 18, 2016

(65) Prior Publication Data
US 2016/0192972 A1 Jul. 7, 2016

Related U.S. Application Data (62) Division of application No. 13/798,880, filed on Mar. 13, 2013, now Pat. No. 9,295,528.

(51) Int. Cl.
| *A61B 90/10* | (2016.01) |
| *A61B 90/11* | (2016.01) |
| *A61B 90/50* | (2016.01) |
| *A61B 17/88* | (2006.01) |
| *A61F 2/46* | (2006.01) |
| *A61B 90/20* | (2016.01) |
| *A61B 90/57* | (2016.01) |
| *A61B 17/00* | (2006.01) |

(52) U.S. Cl.
CPC ...... *A61B 17/8805* (2013.01); *A61B 17/8819* (2013.01); *A61B 17/8855* (2013.01); *A61B 90/10* (2016.02); *A61B 90/11* (2016.02); *A61B 90/20* (2016.02); *A61B 90/50* (2016.02); *A61B 90/57* (2016.02); *A61F 2/4601* (2013.01); *A61B 2017/00557* (2013.01)

(58) Field of Classification Search
CPC .......... A61B 90/10; A61B 90/11; A61B 90/50
See application file for complete search history.

(56) References Cited

U.S. PATENT DOCUMENTS

| 3,017,887 A | 1/1962 | Heyer |
| 5,405,330 A | 4/1995 | Zunitch et al. |
| 5,681,325 A | 10/1997 | Hasson |
| 5,776,143 A | 7/1998 | Adams |
| 5,810,712 A | 9/1998 | Dunn |
| 5,865,817 A | 2/1999 | Moenning et al. |
| 6,039,725 A | 3/2000 | Moenning et al. |
| 6,110,182 A | 8/2000 | Mowlai-Ashtiani |
| 6,287,281 B1 | 9/2001 | Nishtala et al. |

(Continued)

*Primary Examiner* — Nicholas W Woodall (57) ABSTRACT

A device including a first member extending along an axis between a first end and a second end. The first end includes a first portion spaced apart from a second portion by a gap extending parallel to the axis. An inner surface of the first portion and an inner surface of the second portion defining a cavity. A pivoting member is movably disposed in the cavity and includes an inner surface defining a passageway. A second member is disposed within the passageway. The pivoting member is movable between a first orientation such that the gap has a first width and the pivoting member is rotatable to a selected trajectory relative to the axis and a second orientation such that the gap has a second width that is less than the first width and the second member is fixed in the selected trajectory. Methods of use are disclosed.

4 Claims, 6 Drawing Sheets

(56) References Cited

U.S. PATENT DOCUMENTS

| | | |
|---|---|---|
| 6,488,664 B1 | 12/2002 | Solomon et al. |
| 8,277,476 B2 | 10/2012 | Taylor et al. |
| 2014/0276561 A1 | 9/2014 | Arthur et al. |
| 2014/0276875 A1 | 9/2014 | Arthur et al. |
| 2014/0277209 A1 | 9/2014 | Arthur et al. |
| 2014/0277210 A1 | 9/2014 | Arthur et al. |

FIG. 8

DEVICE FOR PERFORMING A SURGICAL PROCEDURE AND METHOD

TECHNICAL FIELD

The present disclosure generally relates to medical devices for the treatment of musculoskeletal structures, and more particularly to a surgical system and method that include a device configured to hold a surgical instrument while a surgical procedure is performed.

BACKGROUND

Height loss is commonly associated with fractures, such as, for example, spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty utilizing a bone void filler, such as, for example, bone cement with balloon catheter technology. The kyphoplasty procedure restores height of the collapsed spinal one which diminishes associated back pains.

Kyphoplasty procedures may also be used to treat fractures in other areas of a patient's body, such as, for example, a distal radius of the patient. To treat a distal radius fracture using a kyphoplasty procedure, an inflatable bone tamp (IBT) is utilized. The IBT is used to percutaneously reduce comminuted, articular depressions in a controlled manner. Fracture morphologies, such as, for example, "die-punch" fractures are especially suited for correction by an IBT. IBTs are deployed to a surgical site, such as, for example, a bone defect through a working cannula. IBTs create well-defined voids. After the void is created by the IBT, the IBT is removed from the cannula and a material, such as, for example a bone void filler is delivered through the cannula and into the void. The bone void filler may be used in conjunction with percutaneous pins, ex-fixes, screws and/or plates for fracture fixation.

In conventional kyphoplasty a procedure, the IBT is inserted adjacent the bone defect by inserting the IBT through a cannula. An inflatable member of the IBT is expanded to create a void in or adjacent the bone defect. After the IBT creates the void, the IBT is removed from the cannula and a bone void filler is delivered through the cannula to the void in order to at least partially fill the void. It is therefore important that the cannula be properly oriented with respect to the bone defect. In conventional kyphoplasty procedures, the cannula is held at a desired trajectory by a physician or physician's assistant, so that the IBT or bone void filler may be delivered through the cannula to a location adjacent the bone defect or void created by the IBT.

Percutaneous delivery of IBT or bone filler material through the cannula to a bone defect or bone void can be difficult. For example, the IBT or bone void filler material may get stuck in the cannula. Furthermore, the distal end of the cannula must be positioned adjacent to the bone defect or bone void to allow the IBT or bone void filler to be delivered through the cannula to the bone defect or bone void. There is often little soft tissue and/or bony anatomy to hold the cannula in a stable position during delivery of the IBT or bone filler material. To stabilize the cannula, a surgical assistant is often required to provide an extra pair of hands to hold the cannula while a surgeon delivers the IBT or the bone filler material to the bone defect or bone void through the cannula. The present disclosure provides a device that acts as a second pair of hands to hold the cannula at a fixed trajectory to ensure that the cannula is properly positional relative to the bone defect or bone void. This disclosure describes an improvement over these prior art technologies.

SUMMARY

Accordingly, a surgical system and method for correction of a bone injury or disorder are provided. In one embodiment, in accordance with the principles of the present disclosure, the surgical system includes a device for performing a surgical procedure. The device includes a first member extending along a longitudinal axis between a first end and a second end. The first end includes a first portion spaced apart from a second portion by a gap extending parallel to the longitudinal axis. An inner surface of the first portion and an inner surface of the second portion defining a cavity. A pivoting member is movably disposed in the cavity and includes an inner surface defining a passageway. A second member is disposed within the passageway. The pivoting member is movable between a first orientation such that the gap has a first width and the pivoting member is rotatable to a selected trajectory relative to the longitudinal axis and a second orientation such that the gap has a second width that is less than the first width and the second member is fixed in the selected trajectory.

In one embodiment, in accordance with the principles of the present disclosure, the surgical system includes a device comprising a first member extending along a longitudinal axis between a first end and a second end. The first end includes a first portion spaced apart from a second portion by a gap extending parallel to the longitudinal axis. An inner surface of the first portion and an inner surface of the second portion define a substantially spherical cavity. The first portion includes a post extending parallel to the longitudinal axis and the second portion includes a hook configured to engage the post to fix the first portion relative to the second portion. A substantially spherical pivoting member is movably disposed in the cavity and includes an inner surface defining a passageway. The cavity and the pivoting member define a ball and socket joint. A second member is disposed within the passageway and includes an inner surface defining a second passageway having an inflatable bone tamp, a bone void filler, bone void filler tool or working cannula disposed therein. The voting member is movable between a first orientation such that the gap has a first width and the pivoting member is rotatable to a selected trajectory relative to the longitudinal axis and a second orientation such that the gap has a second width that is less than the first width and the second member is fixed in the selected trajectory. The hook is spaced apart from the post when the pivoting member is in the first orientation and the hook engages the post when the pivoting member is in the second orientation.

In one embodiment, in accordance with the principles of the present disclosure, a method for repairing a bone is provided. The method comprises the steps of: providing a device comprising: a first member extending along a longitudinal axis between a first end and a second end, the first end including a first portion spaced apart from a second portion by a gap having a first width and extending parallel to the longitudinal axis, the first portion including a post extending parallel the longitudinal axis and the second portion including a hook configured to engage the post to fix the first portion relative to the second portion, an inner surface of the first portion and an inner surface of the second portion defining a cavity, a pivoting member movably disposed in the cavity including an inner surface defining a passageway, and a second member disposed within the passageway; creating an access path to a defect in a bone; inserting the second end of the first member through the access path; inserting a second member into the passageway; rotating the pivoting member to a selected trajectory relative to the longitudinal axis such that a distal end of the second member is positioned adjacent the bone defect; and engaging the hook with the post such that the gap has a second width that is less than the first width and the second member is fixed in the selected trajectory.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of fractures, depressions and breaks. For example, the surgical system and method include a device configured to hold a surgical instrument while performing a surgical procedure to treat a bone defect, such as, for example a fracture.

In one embodiment, the system and method include a device configured to hold a cannula having a ball and socket configuration. The ball is configured to interface with a socket in a tail of the device. The tail has a latch at a distal end configured to tighten the socket around the ball. The tail also has a hinge with strain relief to lighten around the ball.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, balloons that are preformed to have different sizes and shapes.

It is envisioned that the present disclosure may be employed to treat bones, such as, for example, spinal bones or arm bones. It should be understood that the present principles are applicable to any bone structures, including but not limited to bones of the spine, legs, feet, hands, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral. etc. approaches in the arm, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system for holding a surgical instrument while a surgical procedure is performed. The disclosure also includes a description of related methods of employing the disclosed surgical system. Alternate embodiments are also disclosed. Reference will now be made in detail to the exemplary embodiments of the present disclosure, which are illustrated in the accompanying figures. Turning now to FIGS. 1-5, there are illustrated components of a surgical system, such as, for example, a surgical system 30 and embodiments in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open, mini-open or minimally invasive surgical technique to treat a bone defect, such as, for example a fracture. System 30 includes a tail, such as, for example, a first member 32 extending along a longitudinal axis A between a first end 34 and a second end 36. End 34 includes a first portion 38 spaced apart from a second portion 40 by a gap 42 extending parallel to axis A. It is envisioned that gap 42 may be disposed at alternate orientations relative to axis A, such as, for example, perpendicular and/or other angular orientations such as acute or obtuse and/or may be offset or staggered and/or may be disposed at alternative angular orientations relative to axis A, depending on the requirements of a particular application. In one embodiment, portions 38, 40 are resiliently biased away from one another.

An inner surface 44 of portion 38 defines a first hemispherical chamber 46 and an inner surface of portion 40 defines a second hemispherical chamber 50. Chambers 46, 50 define a substantially spherical cavity 52 extending transverse to axis A. It is envisioned that all or only a portion of chamber 46, chamber 50 and/or cavity 52 may be variously configured and dimensioned, such as, for example, planar, concave, convex, hemispherical, spherical, poygonal, irregular, uniform, non-uniform, staggered, tapered, consistent or variable, depending on the requirements of a particular application. It is further envisioned that cavity 52 may be disposed at alternate orientations relative to A, such as, for example, perpendicular and/or other angular orientations such as acute or obtuse and/or may be offset or staggered and/or may be disposed at alternative angular orientations relative to axis A, depending on the requirements of a particular application.

Figure 1:
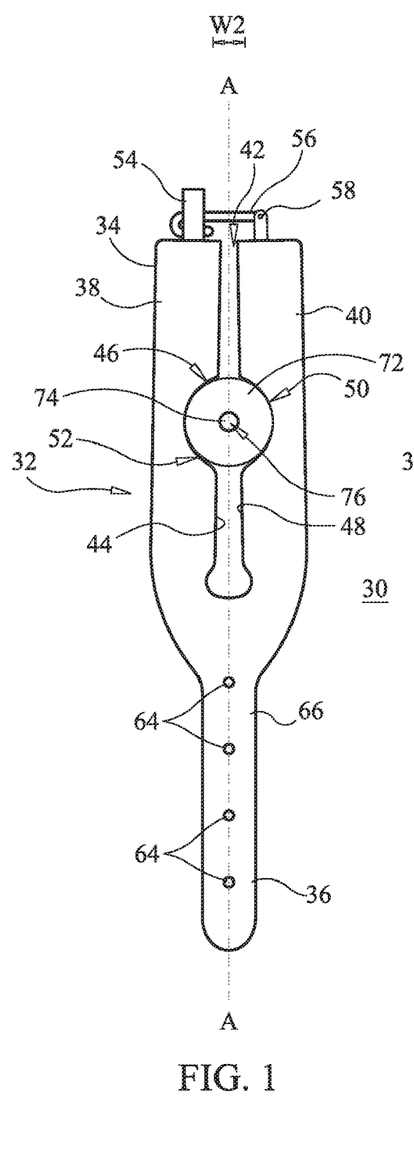
FIG. 1 is a frontal view of one embodiment of components of a system in accordance with the principles of the present disclosure.
Figure 2:
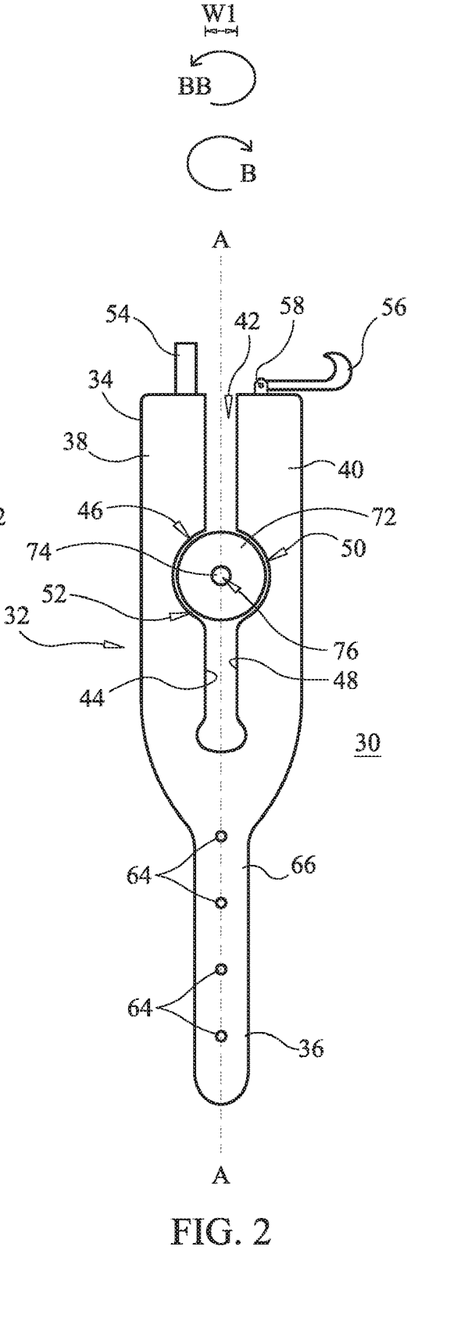
FIG. 2 is a frontal view of one embodiment of the system shown in FIG. 1 in accordance with the principles of the present disclosure.

In one embodiment, shown in FIGS. 1 and 2, portion 38 includes a post 54 extending parallel axis A and portion 40 includes a hook 56 configured to engage post 54 to fix portion 38 relative to portion 40. Hook 56 is disposed on a column 58 extending parallel to axis A and is rotatable relative to column 58 in a direction shown by arrow B or a direction shown by arrow BB to engage post 54. This configuration may be reversed. That is, portion 40 can include post 54 and portion 38 can include hook 56 and column 58. It is envisioned that post 54 and/or column 58 may be disposed at alternate orientations relative to axis A, such as, for example, perpendicular and/or other angular orientations such as acute or obtuse and/or may be offset or staggered and/or may be disposed at alternative angular orientations relative to axis A, depending on the requirements of a particular application. It is further envisioned that portion 38 may be fixed relative to portion 40 in alternate fixation configurations, such as, for example, friction fit, pressure fit, locking protrusion/recess, locking keyway, threaded engagement, latch and/or adhesive.

Figure 3:
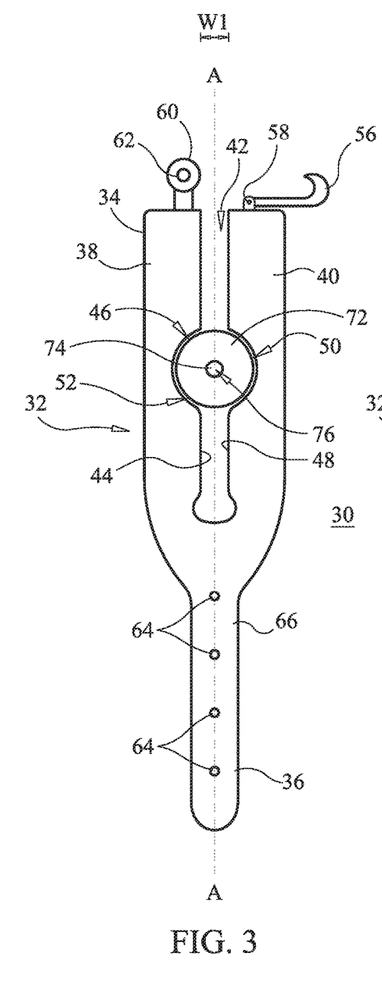
FIG. 3 is a frontal view of one embodiment embodiment of the system shown in FIG. 1 in accordance with the principles of the present disclosure.
Figure 4:
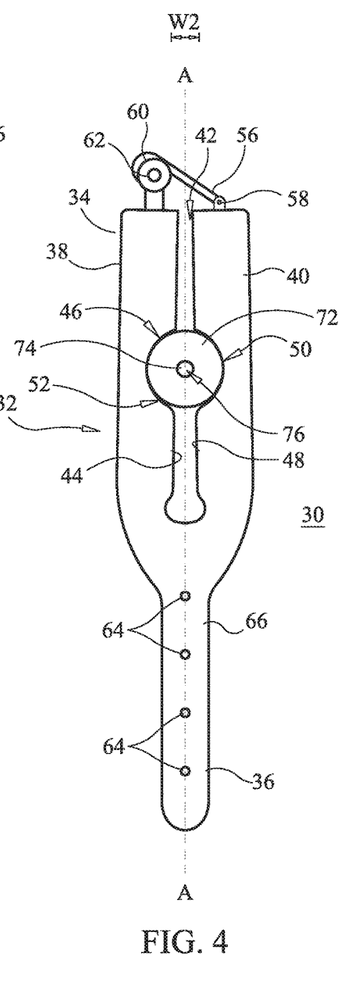
FIG. 4 is a side, cross sectional view of components of the system shown in FIG. 1.

In one embodiment, shown in FIGS. 3 and 4, portion 38 includes an eyelet 60 having an inner surface defining a hole 62 extending transverse to axis A. Hook 56 is configured for disposal in hole 62 to fix portion 38 relative to portion 40. This configuration may be reversed. That is, portion 40 may include eyelet 60 and portion 38 may include crook 56. It is envisioned that hole 62 may be disposed at alternate orientations relative to axis A, such as, for example, perpendicular and/or other angular orientations such as acute or obtuse and/or may be offset or staggered and/or may be disposed at alternative angular orientations relative to axis A, depending on the requirements of a particular application.

End 36 includes an aperture 64 extending through a first surface 66 and a second surface 68 of end 36. Aperture 64 is configured to receive an engagement device, such as, for example a pin or K-wire 70 configured to fix member 32 relative to the anatomy of a patient. It is envisioned that end 36 may include one or a plurality of apertures 64. It is further envisioned that system 30 may include one or a plurality of pins/K-wires 70, corresponding to the number of apertures 64. In the embodiment shown in FIGS. 4 and 5, end 36 includes apertures 64 extending perpendicular to axis A that alternate with apertures 64 extending at an acute angle relative to axis A. However, it is contemplated that the apertures 64 that extend at an acute angle relative to axis A may be positioned proximally of the apertures 64 that extend perpendicular to axis A. It is further contemplated that the apertures 64 that extend at an acute angle relative to axis A may be positioned distally of the apertures 64 that extend perpendicular to axis A. It is envisioned that apertures 64 may be disposed through angular ranges in various orientations relative to axis A, such as, for example, transverse or perpendicular and/or other angular orientations such as acute or obtuse, and/or may be offset or staggered. In some embodiments, apertures 64 and/or pins/K-wires 70 may be rough, textured, porous semi-porous, dimpled and/or polished to facilitate engagement between apertures 64 and pins/K-wires 70.

A substantially spherical pivoting member 70 is movably disposed in cavity 52 and includes an inner surface 74 defining a passageway 76. Cavity 52 and member 72 define a ball and socket joint. Passageway 76 has a cylindrical cross sectional configuration and a uniform diameter throughout the length of passageway 76. It is envisioned that all or only a portion of member 70 may be variously configured and dimensioned, such as, for example, planar, concave, convex, hemispherical, spherical, polygonal, irregular, uniform, non-uniform, staggered, tapered, consistent or variable, depending on the requirements of a particular application. It is further envisioned that all or only a portion of passageway 76 may have alternate cross section configurations, such as, for example, oval, oblong, triangular, square, polygonal, irregular, uniform, non-uniform, offset, staggered, undulating, arcuate, variable and/or tapered, depending on the requirements of a particular application.

A second member, such as, for example a cannula 78 is disposed within passageway 76. In some embodiments, surface 74 includes a deformable material, such as, for example, silicone or elastomer (e.g., synthetically produced butyl rubber or neoprene or a natural rubber) disposed about passageway 76 to facilitate engagement of cannula 78 with member 72. Cannula 78 includes an surface 80 defining a second passageway 82 configured for disposal of an inflatable bone tamp or a bone filler material in order to deliver the same to a surgical site, such as, for example a bone defect. Passageway 82 has a cylindrical cross sectional configuration and a uniform diameter throughout the length of passageway 82. In some embodiments, member 70 comprises a deformable material, such as, for example, polypropylene such that surface 74 provides a friction fit with an outer surface of cannula 78. It is envisioned that or only a portion of passageway 82 may have alternate cross section configurations, such as, for example, oval, oblong, triangular, square, polygonal, irregular, uniform, non-uniform, offset, staggered, undulating, arcuate, variable and/or tapered, depending on the requirements of a particular application.

Member 72 is movable between first orientation such that gap 42 has a first width W1, as shown in FIG. 2, and member 72 is rotatable to a selected trajectory relative to axis A and a second orientation such gap 42 has a second width W2, as shown in FIG. 1, that is less than first width W1 and cannula 78 is fixed in the selected trajectory. That is, as member 72 moves from the first orientation to the second orientation, surface 44 exerts a clamping force on member 72 to fix member 72 relative to member 32.

In the embodiment including hook 56 and post 54, hook 56 is spaced apart from post 54 when member 72 is in the first orientation, as shown in FIG. 2, and hook 56 engages post 54 when member 72 is in the second orientation, as shown in FIG. 1. In the embodiment including hook 56 and eyelet 60, hook 56 is spaced apart from eyelet when member 72 is in the first orientation, as shown in FIG. 3, and hook 56 is disposed within eyelet 60 when member 72 is in the second orientation, as shown in FIG. 4.

Figure 5:
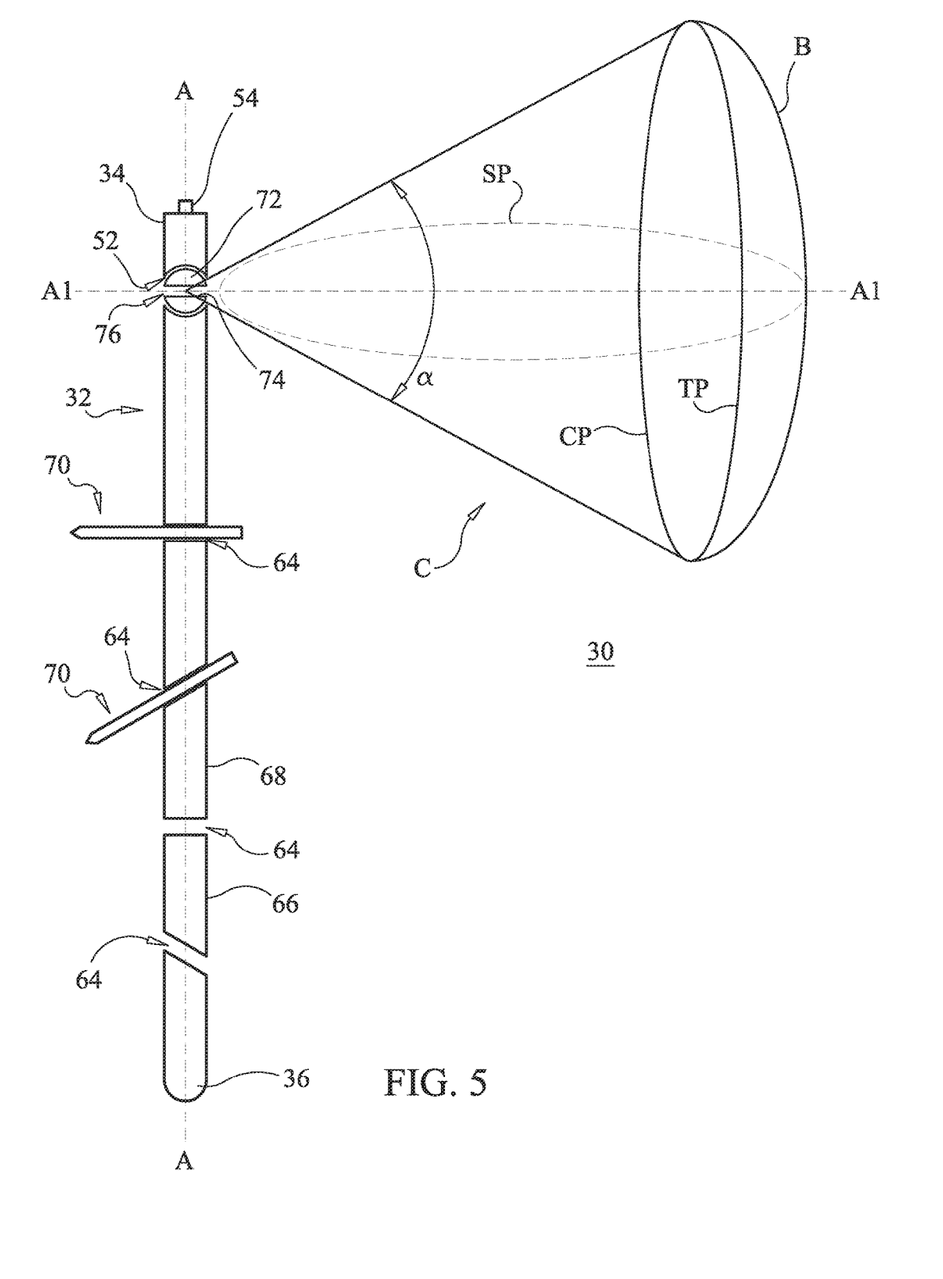
FIG. 5 is a side, cross sectional view of components of the system shown in FIG. 1.
Figure 6:
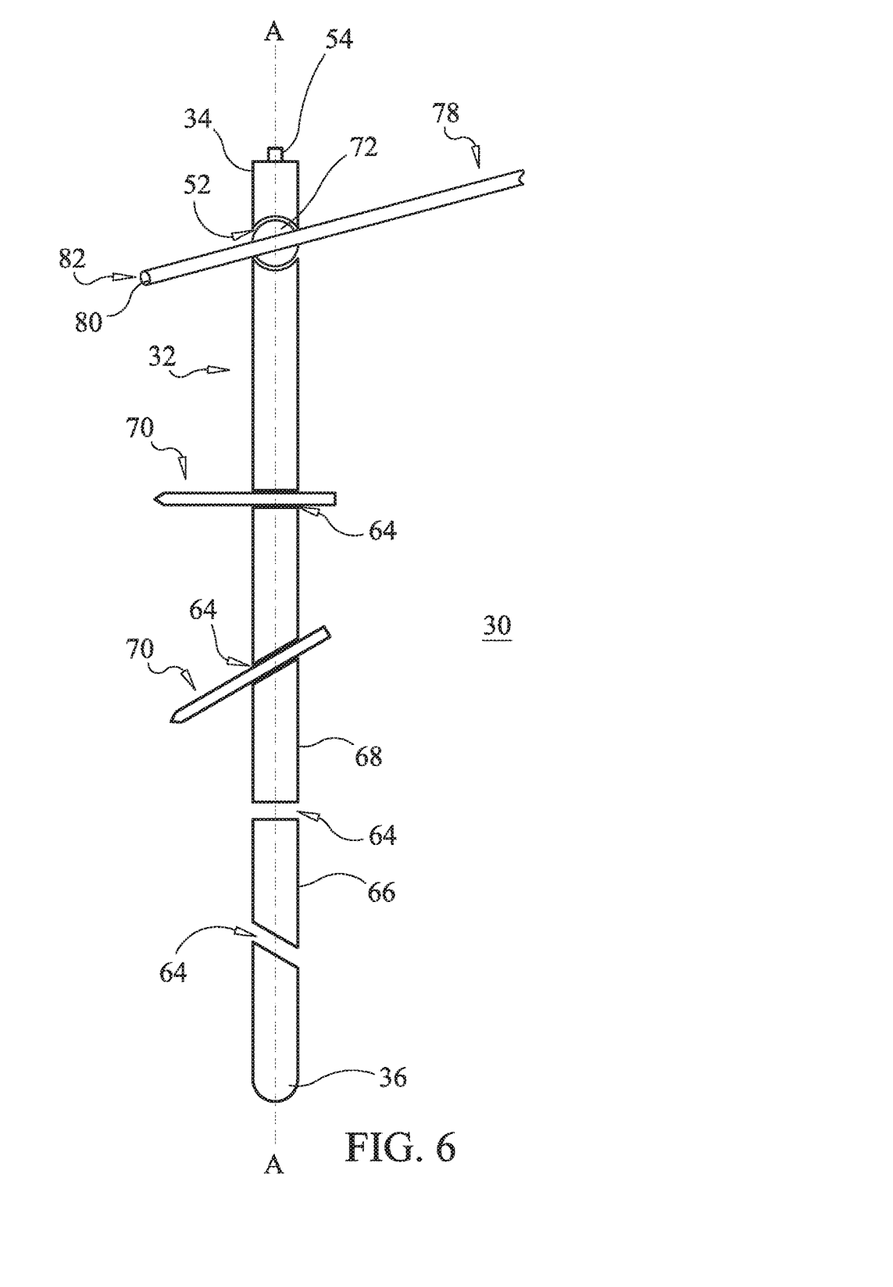
FIG. 6 is a side, cross sectional view of components of a system in accordance with the principles of the present disclosure.

When member 72 is in the first orientation, passageway 76 is rotatable to a selected angle through and within angular range $\alpha$ relative to axis a in a plurality of planes that lie in a cone configuration C, as shown in FIG. 5. The area and/or volume defined by cone C, which includes the configuration disposed between a transverse axis A1 and a circular base B, is defined by the range of motion of passageway 76 axis A1. The plurality of planes includes a locus of all straight line segments that join axis A1 and base B. For example, passageway 76 is separately rotatable to a selected angle within angular range $\alpha$ in each plane corresponding to a particular straight line segment that lies in cone configuration C. It is contemplated that passageway 76 may rotatable through the individual diameters, chords, section and/or radii of base b and/or other portions of cone C. In one embodiment, passageway 76 is rotatable to a selected angle within angular range $\alpha$ in a sagittal plane (SP), corresponding to a particular plane that lies in cone C. In one embodiment, passageway 76 is rotatable to a selected angle within angular range $\alpha$ in a transverse plane (TP), corresponding to a particular plane that lies in cone C. In one embodiment, passageway 76 is rotatable to a selected angle within angular range $\alpha$ in a coronal plane (CP), corresponding to a particular plane that lies in cone C.

Figure 7:
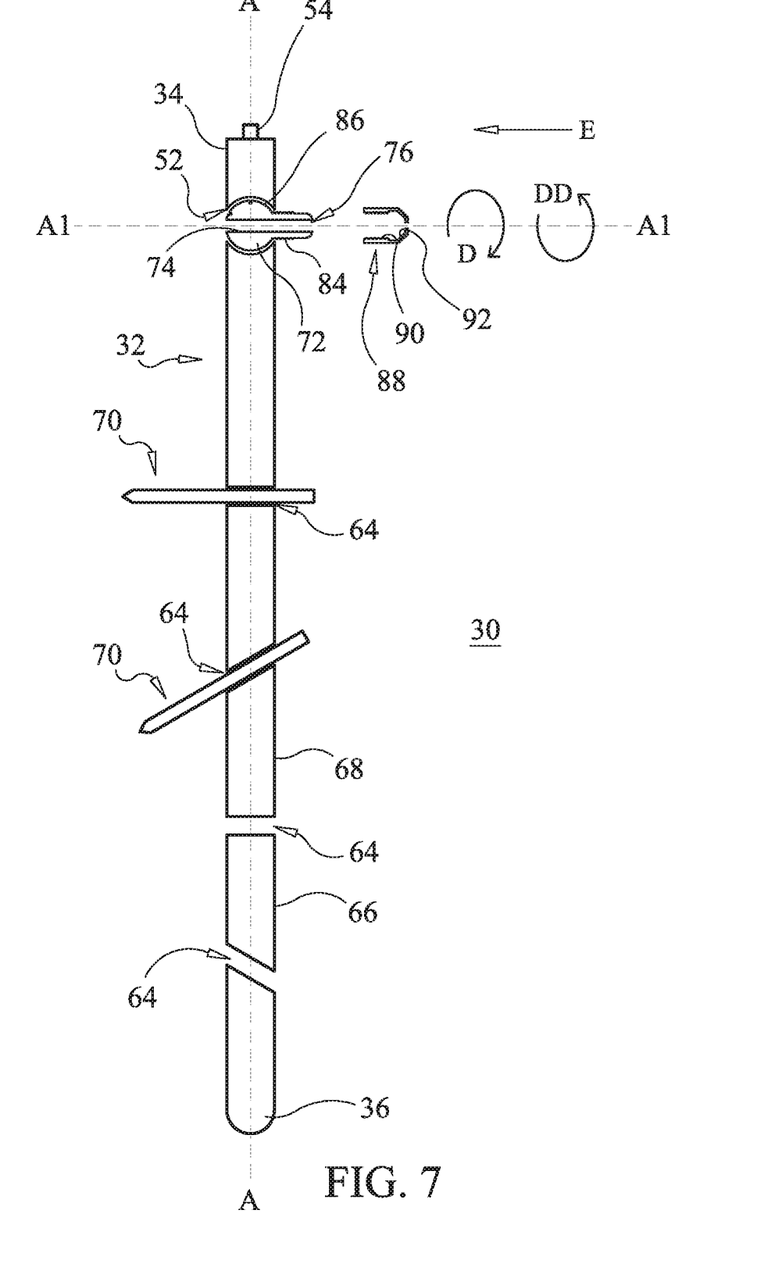
FIG. 7 is a side, cross sectional view of components of a system in accordance with the principles of the present disclosure.
Figure 8:
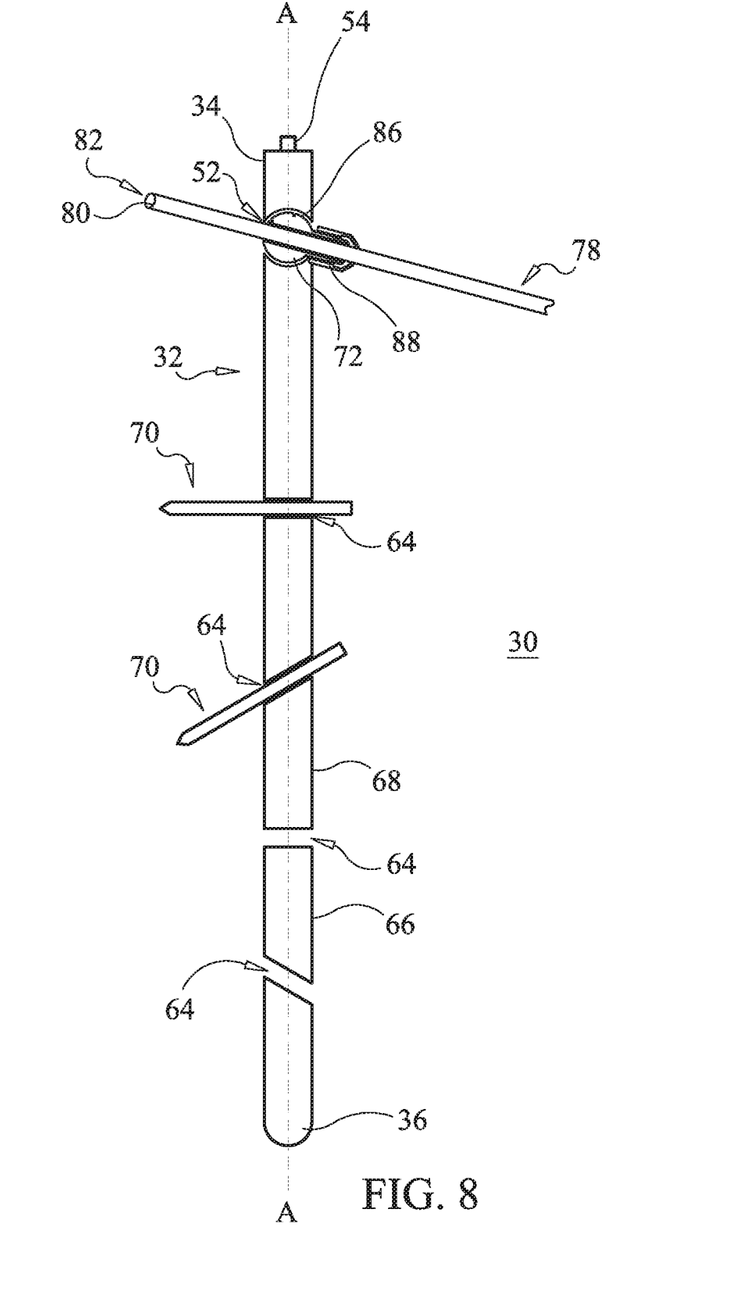
FIG. 8 is a side, cross sectional view of the system shown in FIG. 7.

In one embodiment, shown in FIGS. 7 and 8, member 72 includes a collet 84 extending from a substantially spherical ball 6. Passageway 76 extends through both collet 84 and ball 86. Collet 84 includes an outer surface having a uniform diameter along the length of collet 84. At least a portion of the outer surface of collet 84 is threaded. System 30 includes a cap 88 having a first end including a threaded inner surface 90 and a second end having with an angled inner surface 92 that is free of threads. Threaded inner surface 90 is configured to engage the threaded outer surface of collet 84 to engage cap 88 with collet 84. As threaded inner surface 90 engages the threaded outer surface of collet 84, cap 88 is rotated in the direction shown by arrow D or arrow DD such that cap 88 translates relative to collet 84 in the direction shown by arrow E. As cap 88 translates in the direction shown by arrow E, angled inner surface 92 engages the outer surface of collet 84 causing inner surface 74 to engage cannula 78. Because surface 92 is angled, rotation of cap 88 in the direction shown by arrow D or arrow DD allows for incremental tightening of surface 74 about cannula 78 such that a restrictive force applied to cannula 78 can be adjusted by altering the amount of rotation of cap 88. When 90 is fully threaded with the threaded outer surface of collet 84, cannula 78 becomes fixed relative to member 72. That is, cap 88 is movable between a first orientation such that threaded inner surface 90 is spaced apart from the threaded outer surface of collet 84, as shown in FIG. 7 and cannula 78 is movably disposed within passageway 76 and a second orientation such that threaded inner surface 90 engages the threaded outer surface of collet 84 and cannula 78 is fixed within passageway 76.

In assembly, operation and use, system 30 is employed with a surgical procedure, such as, for a correction or treatment of a bone defect, such as, for example, a fracture. It is contemplated that one or all of the components of system 30 can be delivered or implanted as a pre-assembled device or can be assembled in situ. System 30 may be completely or partially revised, removed or replaced. For example, system 30 can be employed with a surgical correction treatment of an applicable condition or injury of an affected portion of a patient, such as, for example, a distal radius or a vertebra. It is envisioned that system 30 may also be used to treat other affected portions of the patient, such as, for example, a calcaneus bone, bones of the feet or hands, bones of the legs, etc.

In use, to treat a fracture, a medical practitioner obtains access to a surgical site including the fractured bone in any appropriate manner, such as through incision and retraction of tissues. In one embodiment, a drill is employed to remove bone tissue to provide access to a repair site. It is envisioned that system 30 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 30 is determined according to the configuration, dimension and location of a selected section of the bone fracture and the requirements of a particular application.

An incision is made in the body of a patient and a cutting instrument (not shown) creates a surgical pathway for implantation of components of system 30. This may include the use of a cannula or other device. A preparation instrument (not shown) can be employed to prepare tissue surfaces, as well as for aspiration and irrigation of a surgical region according to the requirements of a articular surgical application.

Pins/K-wires 70 are positioned within through apertures 64 and are disposed in the anatomy of the patient, such as, for example, tissue, to fix or stabilize member 32 relative to the anatomy of the patient, with cannula 78 positioned within passageway 76. Member 32 is stabilized with pins/K-wires 70.

In embodiments, that include cap 88, threaded inner surface 90 is aligned with the threaded outer surface of collet 84. Cap 88 is rotated in the direction shown by arrow D or arrow DD such that threaded inner surface 80 engages the threaded outer surface of collet 84 and cap 88 translates relative to collet 84 in the direction shown by arrow E. Cap 88 is translated in the direction shown by arrow E until angled inner surface 92 engages the outer surface of collet 84 causing inner surface 74 to engage cannula 78 such that cannula 78 is fixed relative to member 72. Member 72 is then rotatable to a selected trajectory relative to axis A such that cannula 78 is positioned adjacent the bone disorder. Member 72 is then moved from the first orientation to the second orientation such that cannula 78 is fixed in the selected trajectory.

An inflatable bone tamp may then be delivered through cannula 78 to a location adjacent the bone disorder or defect. The inflatable bone tamp may then be expanded to create a cavity or void in the bone by delivering a material, such as, for example, saline, a contrast solution or compressed air into an expandable member of the inflatable bone tamp, such as, for example, a balloon, to move the balloon from an unexpanded configuration to an expanded configuration. As the balloon moves from the unexpanded configuration to the expanded configuration, the balloon creates a void in the bone having the defect or disorder. Member 72 maintains cannula 78 in a stabilized orientation with respect to the body such that a single practitioner can insert the inflatable bone tamp through cannula 78 and operate the inflatable bone tamp in a steady manner. That is, cannula 78 remains at the selected trajectory such that a distal end of cannula 78 is positioned adjacent the bone defect, without the need for a physician or physician's assistant to hold cannula 78.

After the void is formed in the bone, the inflatable bone tamp is removed from cannula 78. Bone filler material is then delivered through cannula 78 or a separate delivery tool configured to deliver bone filler material disposed in passageway 76 and into the void so as to at least partially fill the void and realign fragments of the fracture and/or elevate collapsed bone to its proper height. Member 72 maintains cannula 78 in a stabilized orientation with respect to the body such that a single practitioner can administer the bone filler material in a steady manner. That is, cannula 78 remains at the selected trajectory such that a distal end of cannula 78 is positioned adjacent the bone defect, without the need for a physician or physician's assistant to hold cannula 78. It is envisioned that the bone filler material may include autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables.

In one embodiment, system 30 includes an agent, which may be disposed, packed or layered within, on or about the components and/or surfaces of the components of system 30, such as, for example, members 32, 72 or cannula 78. It is envisioned that the agent may include bone growth promoting material, such as, for example, bone graft to enhance fixation of the fixation elements with the bone in need of repair. It is further contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of system 30 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these embodiments, which, nevertheless, fall within the spirit of the present disclosure, whose scope is defined by the claims set forth below.

What is claimed is:

1. A method for treating a bone defect, the method comprising the steps of:
    providing a device comprising: a first member extending along a longitudinal axis between a first end and a second end, the first end including a first portion spaced apart from a second portion by a gap having a first width and extending parallel to the longitudinal axis, the first portion including a post extending parallel the longitudinal axis and the second portion including a hook configured to engage the post to fix the first portion relative to the second portion, an inner surface of the first portion and an inner surface of the second portion defining a cavity, a pivoting member movably disposed in the cavity including an inner surface defining a passageway, and a second member disposed within the passageway;
    creating an access path to a defect in a bone;
    inserting the second end of the first member through the access path;
    inserting a second member into the passageway;
    rotating the pivoting member to a selected trajectory relative to the longitudinal axis such that a distal end of the second member is positioned adjacent the bone defect; and
    engaging the hook with the post such that the gap has a second width that is less than the first width and the second member is fixed in the selected trajectory.

2. A method according to claim 1, wherein the bone defect is a fracture in a distal radius of a human patient and the second member is a cannula.

3. A method according to claim 1, wherein the second member includes an inner surface defining a second passageway, the method further comprising:
    inserting an inflatable bone tamp into the second passageway such that at least a portion of the inflatable bone tamp is disposed adjacent the bone defect;
    and creating a void in the bone using the inflatable bone tamp.

4. A method according to claim 3, further comprising:
    removing the inflatable bone tamp from the second passageway;
    and delivering a bone void filler through the second passageway to the void.

* * * * *

UNITED STATES PATENT AND TRADEMARK OFFICE
CERTIFICATE OF CORRECTION

PATENT NO. : 10,258,398 B2  
APPLICATION NO. : 15/046654  
DATED : April 16, 2019  
INVENTOR(S) : Arthur et al.

Page 1 of 2

It is certified that error appears in the above-identified patent and that said Letters Patent is hereby corrected as shown below:

In the Specification

In Column 1, Line 3, insert -- CROSS-REFERENCE TO RELATED APPLICATIONS
This application is a Divisional of U.S. Patent Application Ser. No. 13/798,880, filed on March 13, 2013, which is incorporated herein by reference herein, in its entirety. -- above "TECHNICAL FIELD", as a new paragraph.

In Column 1, Lines 23-24, delete "spinal one" and insert -- spinal bone --, therefor.

In Column 2, Line 4, delete "positional" and insert -- positioned --, therefor.

In Column 2, Line 47, delete "voting" and insert -- pivoting --, therefor.

In Column 3, Line 26, delete "embodiment embodiment" and insert -- embodiment --, therefor.

In Column 3, Line 62, delete "lighten" and insert -- tighten --, therefor.

In Column 4, Line 1, delete "preformed" and insert -- performed --, therefor.

In Column 4, Line 16, delete "antero-lateral." and insert -- antero-lateral, --, therefor.

In Column 5, Line 33, delete "incorporated of" and insert -- Incorporated of --, therefor.

In Column 5, Line 54, delete "sulfate" and insert -- sulfate, --, therefor.

In Column 6, Lines 23-24, delete "poygonal," and insert -- polygonal, --, therefor.

In Column 6, Line 27, delete "A," and insert -- axis A, --, therefor.

In Column 6, Line 58, delete "cook 56." and insert -- hook 56. --, therefor.

Signed and Sealed this  
Fifteenth Day of October, 2019

Andrei Iancu  
*Director of the United States Patent and Trademark Office*

In Column 7, Line 21, delete "porous" and insert -- porous, --, therefor.

In Column 7, Line 47, delete "an surface" and insert -- an inner surface --, therefor.

In Column 7, Line 56, delete "that or" and insert -- that all or --, therefor.

In Column 7, Line 62, delete "between first" and insert -- between a first --, therefor.

In Column 8, Line 39, delete "ball 6." and insert -- ball 86. --, therefor.

In Column 9, Line 38, delete "articular" and insert -- particular --, therefor.